United States Patent [19]

Gangneux

[11] 4,256,901
[45] Mar. 17, 1981

[54] PHTHALONE DERIVATIVES UTILIZABLE AS PIGMENTS

[75] Inventor: Philippe Y. E. Gangneux, Bihorel, France

[73] Assignee: Produits Chimiques Ugine Kuhlmann, Courbevoie, France

[21] Appl. No.: 1,042

[22] Filed: Jan. 4, 1979

[30] Foreign Application Priority Data

Jan. 13, 1978 [FR] France .................. 78 00889

[51] Int. Cl.³ .......................................... C07D 235/04
[52] U.S. Cl. .................. 548/268; 546/271; 548/161; 548/328; 548/330; 548/334
[58] Field of Search ............ 548/330, 328, 334, 161, 548/268; 546/271

[56] References Cited
U.S. PATENT DOCUMENTS 2,894,952   7/1959   Amstutz et al. ................. 548/334

FOREIGN PATENT DOCUMENTS 2107504   9/1971   Fed. Rep. of Germany .
1445003   5/1966   France .
1517719   2/1968   France ................................. 548/328
48-95417  3/1972   Japan .................................. 548/328
48-3523   1/1973   Japan .................................. 548/328

OTHER PUBLICATIONS

Junek et al., Chem. Ber., 110, 2276–2282, (1977).

*Primary Examiner*—Ethel G. Love
*Attorney, Agent, or Firm*—Beveridge, DeGrandi, Kline & Lunsford

[57] ABSTRACT

Phthalones derived from benzimidazole can be represented by one of the following general formulas:

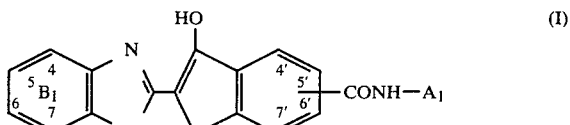

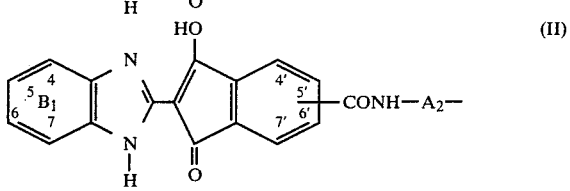

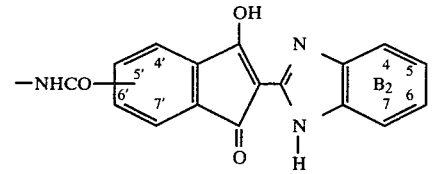

in which $A_1$ and $A_2$ each represents an aliphatic, alicyclic, aromatic or heterocyclic radical, possibly substituted by one or more nonsolubilizing substituents, and each of the benzene nuclei $B_1$ and $B_2$ can bear one or two substituents selected from halogen atoms and the lower alkyl, lower alkoxy, nitro, acylamino and aryl groups or be coupled with another benzene nucleus.

These phthalones are valuable pigments for textile printing and for coloring inks, lacquers, paints, varnishes and plastic materials.

10 Claims, No Drawings

PHTHALONE DERIVATIVES UTILIZABLE AS PIGMENTS

The present invention relates to new phthalone derivatives, to procedures for preparing them and to their use as pigments for textile printing and the coloring of ink, lacquer, paint, varnish and plastic materials.

The use of pigments of products obtained by the condensation of 2-methyl benzimidazole or its substituted derivatives with an anhydride, and particularly with tetrachlorophthalic anhydride (Japanese application of Dec. 17, 1970, published under the number 73 03523; Japanese Journal "Shikizai Kyokaishi", 49 (3), 149–151, article by Tagaki et al.) and pyromellitic anhydride (Japanese application of Mar. 24, 1972, published under the number 73 95417), has already been proposed. However, these products do not give complete satisfaction as pigments, either because of the presence of by-products formed by the partial thermal deshydrohalogenation of the polyhalogenated anhydrides or incompletely cycled or rearranged products (particularly in the case of pyromellitic anhydride) or because their implementation or use properties (resistance to migration, solidity in light) are insufficient.

It has now been discovered that new phthalone derivatives can be obtained in a very pure form, which offer excellent thermal stability, as well as very great resistance to weathering and light.

The new derivatives of the present invention, which are insoluble in the usual organic solvents, can be represented by one of the following general formulas:

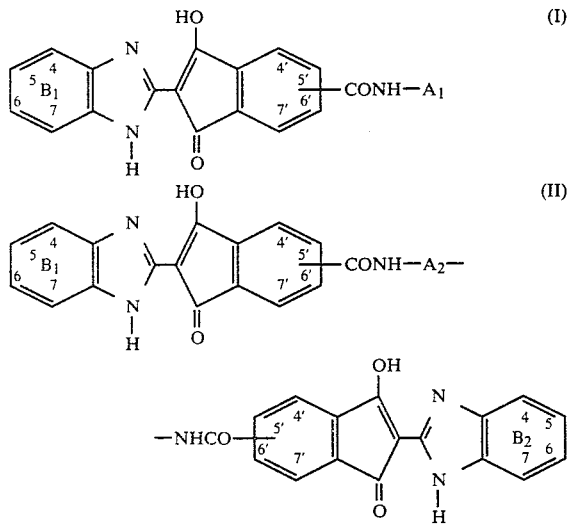

in which $A_1$ and $A_2$ each represents an aliphatic, alicyclic, aromatic or heterocyclic radical, possibly substituted by one or more nonsolubilizing substituents, and each of the benzene nuclei $B_1$ and $B_2$ can bear one or two substituents selected from halogen atoms and lower alkyl, lower alkoxy, nitro, acylamino and aryl groups or be coupled with another benzene nucleus.

Each of the formulas (I) and (II) above constitutes only one of the tautomeric forms possible for the compounds according to the invention; as a matter of fact, positions 1, 4, 5, 1', 4' and 5' are equivalent to positions 3, 7, 6, 3', 7' and 6', respectively.

The aliphatic radical $A_1$ or $A_2$ can be linear or ramified, and it preferably contains from 2 to 10 carbon atoms.

When $A_1$ or $A_2$ is an alicyclic radical, it preferably contains 6 carbon atoms.

When $A_1$ or $A_2$ is an aromatic radical, it may be, for example, a diphenyl radical, a naphthalenic radical, an anthraquinonic radical, possibly substituted by one or two atoms of chlorine or bromine, but particularly a benzene radical, preferably substituted by one or more nonsolubilizing substituents such as a halogen atom (particularly chlorine and bromine) and the lower alkyl, lower alkoxy, nitro, cyano, acylamino (particularly acetylamino and benzoylamino, possibly substituted) or sulfo (as the salt of a divalent metal) groups; the benzene radical can bear up to five substituents in the case of $A_1$ and up to four substituents in the case of the divalent radical $A_2$.

When $A_1$ or $A_2$ represents a heterocyclic radical, it can be monocyclic or polycyclic, contain one or more identical or different heteroatoms such as oxygen, sulfur and, especially, nitrogen, and bear one or more nonsolubilizing substituents such as those disclosed above.

When the benzene nuclei $B_1$ and $B_2$ bear halogen atoms, they can be bromine or iodine, but they are preferably chlorine. The acylamino groups which bear the $B_1$ and $B_2$ nuclei are preferably alkylcarbonylamino groups containing 2 to 4 carbon atoms (particularly acetylamino) or aroylamino groups (particularly benzoylamino, possibly bearing one or two nitro groups). When the $B_1$ nucleus and/or the $B_2$ nucleus bears only a single substituent, it can be fixed in position 4 (=7) or 5 (=6). When two substituents are present on $B_1$ and/or $B_2$, those substituents which can be identical or different, are fixed in position 4,6 (=5,7), in position 4,5 (=6,7) or in position 5,6. In the compounds of formula (II), the possible substituents for the nucleus $B_2$ can be different from those for the nucleus $B_1$; however, the compounds of formula (II), whose two nuclei $B_1$ and $B_2$ are identical, are preferred.

By lower alkyl and lower alkoxy groups, we mean alkyl and alkoxy groups containing from 1 to 4 carbon atoms.

Particularly valuable compounds of formulas (I) and (II) are those in which the radicals —CONH—$A_1$ and —CONH—$A_2$—NHCO— are fixed in positions 5' or 6' and, among those compounds, those whose nuclei $B_1$ and $B_2$ are not substituted or are substituted by a chlorine atom or by one or two methyl groups.

The compounds of formula (I) in which $A_1$ is the 1,2,4-triazole 3-yle or a substituted phenyl radical, and particularly the 2-nitro 4-methyl phenyl, the 3,5-dimethyl phenyl or the 2,4,5-trichloro phenyl radical have been found to be particularly interesting.

Among the dyes of formula (II), those in which $A_2$ is a p-phenylene or a chloro-p-phenylene radical have been found to be particularly advantageous.

Mixtures of compounds of formulas (I) and (II) are also included in the present invention.

The compounds of the invention can be prepared in accordance with one or another of the following procedures.

Procedure A

The first procedure for preparing the compounds of formulas (I) and (II) consists of the following:

(a) Condensing, in an inert solvent and at a temperature of between 120° and 250° C., and preferably between 160° and 230° C., trimellitic anhydride, hemimellitic anhydride or a mixture of said anhydrides and one or more benzimidazoles of the formula:

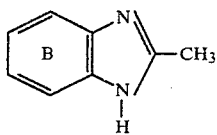 (III)

with the nucleus B having the same meaning as $B_1$ and $B_2$, above; then (b) Transforming the acid or mixture of acids thus obtained, having the formula:

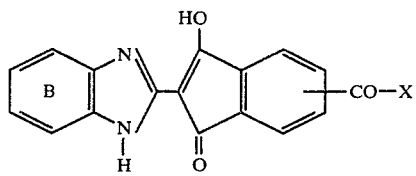 (IV)

in which X represents a hydroxy group into a halogenoformylated derivative (formula IV, with X being chlorine or bromine); and, finally (c) Condensing this derivative with one (or more) $A_1$—$NH_2$ monoamine(s) or $H_2N$—$A_2$—$NH_2$ diamine(s) (amidification reaction).

The successive reactions a, b and c can be carried out without isolating the intermediate products. However, it is preferable to isolate those products.

Procedure B

This procedure, to which Procedure A which leads to very pure products is preferred, consists of condensing one or more benzimidazoles of formula (III) with an anhydride of the formula:

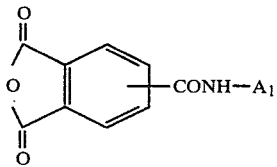 (V)

or with a dianhydride of the formula:

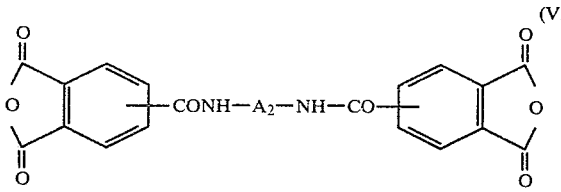 (VI)

in which $A_1$ and $A_2$ have the same meanings as disclosed above.

This reaction is carried out in an inert solvent at a temperature falling between 120° and 250° C., and preferably between 160° and 230° C.

As examples of inert solvents utilizable for carrying out the condensation of the benzimidazole or benzimidazoles of formula (III) either with the trimellitic anhydride and/or the hemimellitic anhydride (stage a of Procedure A) or with an anhydride of formula (V) or a dianhydride of formula (VI) in accordance with Procedure B, nitrobenzene, the xylenes, chlorobenzene, the polychlorobenzenes, α-chloronaphthalene, dimethyl formamide, dimethyl acetamide, formamide, dimethyl sulfoxide and quinoline may be used.

This condensation reaction can also be carried out in the presence of a catalyst. As such, hydrochloric acid, p-toluene sulfonic acid, the xylene-sulfonic acids and the chlorides, acetates or carbonates of monovalent or divalent metals such as zinc chloride and stannous chloride may be used.

As examples of benzimidazoles of formula (III), the following compounds are preferred:
2-methyl benzimidazole
5(6)-nitro 2-methyl benzimidazole
5(6)-chloro 2-methyl benzimidazole
4(7)-chloro 2-methyl benzimidazole
4,5(6,7)-dichloro 2-methyl benzimidazole
5,6-dichloro 2-methyl benzimidazole
2,4(2,7)-dimethyl benzimidazole
2,5(2,6)-dimethyl benzimidazole
2,4,5(2,6,7)-trimethyl benzimidazole
2,5,6-trimethyl benzimidazole
5(6)-methoxy 2-methyl benzimidazole
5(6)-acetylamino 2-methyl benzimidazole
5(6)-phenyl 2-methyl benzimidazole These compounds can be used alone or in mixtures.

Among the compounds that can be used to carry out the halogenformylation of the acids of formula IV (X=OH), the preferred compounds include thionyl chloride, sulfuryl chloride, phosphorus oxychloride and the polychlorides of phosphorus. This reaction can be carried out with or without a solvent, but preferably with an inert solvent such as those enumerated above. The reaction is conducted at a temperature between 100° and 220° C., and preferably between 130° and 170° C.

The amidification reaction (stage c of Procedure A) is carried out in an inert solvent such as those enumerated above at a temperature between 120° and 250° C., and preferably between 140° and 220° C., possibly in the presence of an acceptor (mineral base, or an organic amine such as pyridine).

As examples of $A_1$—$NH_2$ monoamines which can be used alone or in admixture to obtain the compounds of formula (I) according to the invention, the following can be used:
n-hexylamine;
cyclohexylamine;
aniline and its substituted derivatives, such as o-, m- or p-toluidine, p-chloroaniline, 2,5-dichloro aniline, 2,4,5-trichloroaniline, 2-nitro 4-methyl aniline, 2-sulfo 4-methyl aniline (in the form of the salt of any divalent metal), the chloro-nitro anilines, p-anisidine, the xylidines, 4-acetylamino aniline, 2-cyano 4-nitro aniline and 4-bromo aniline;
N-benzoyl m- or p-phenylene diamine, N-(m- or p-aminobenzoyl)-aniline and their derivatives substituted by halogen atoms or nitro, lower alkyl or lower alkoxy groups;
α- or β-naphthyl amine;
2,3 or 4-amino diphenyl;
α- or β-amino-anthraquinone;
the amino-pyridines, 3-amino 1,2,4-triazole, 3(5)phenyl 5(3)-amino pyrazole and 2-amino benzothiazole.

As examples of $H_2N$—$A_2$—$NH_2$ diamines which can be used alone or in mixtures to obtain compounds of formula (II) of the invention, the following can be used:

the o-, m- and p-phenylenediamines and their monochlorinated or polychlorinated, cyanated, brominated, methoxylated, ethoxylated and/or methylated derivatives;

2,6-diamino pyridine;

benzidine and its isomers, such as diphenyline, for example;

1,4 or 1,5 or 2,6 or 2,7-diamino naphthalene;

1,4 or 2,6-diaminoanthraquinone;

4,4'-diamino diphenylamine;

the oxide or the sulfide of 4,4'-diamino diphenyl;

4,4'-diamino benzanilide, 4,4'-diamino benzophenone, 4,4'-diamino diphenylurea;

4,4'-diamino diphenyl-sulfone and 4,4'-diamino diphenylsulfoxide.

It is apparent that a mixture of monoamine and diamine can be used. There is thus obtained a mixture of compounds of formulas (I) and (II).

As was stated above, the three stages of Procedure A can be carried out without isolating the intermediate products. In that case, the procedure is preferably carried out in nitrobenzene, dichlorobenzene or trichlorobenzene since those solvents permit the obtaining of excellent yields for each successive reaction.

The compounds of the invention are most often obtained in a physical form which makes it possible to use them as they are. When it is necessary or when a particular variety is sought, it is possible to submit them to any treatment ordinarily carried out on pigments: dissolving, followed by sulfuric precipitation, permutoid inflation, heating in the presence of organic solvents, grinding, and kneading in the presence, or absence, of mineral salts and/or solvents and/or additives.

The pigments of the invention offer shadings from greenish yellow to dark orange and can be obtained in opaque and transparent forms. They make it possible to color extremely different materials and backgrounds, such as inks, varnishes, paints, rubber, plastics and compositions for the pigmentary printing of textiles, with remarkable coloristic and implementing qualities. Their remarkable heat stability makes them particularly suitable for coloring plastic materials, among which can be mentioned the thermosetting resins and the thermoplastic polymers: for example, alkyd resins, polyester resins, polyurethanes, polyolefins, polystyrene and its copolymers, polyesters, polyamides and polyethers. These polymers can be made use of by hot-pressing, casting, injection, extrusion or any other technique and be used like plastic materials, as films or as fibers.

The following examples illustrate the invention without limiting it. The proportions indicated are by weight unless otherwise stated.

EXAMPLE 1

(1-a) Into 500 parts by volume of trichlorobenzene are introduced 40 parts of trimellitic anhydride and 27.5 parts of 2-methyl benzimidazole. The mixture is heated to reflux and maintained under such conditions for 3 or 4 hours, the water formed by the reaction being distilled should the occasion arise. After cooling to 50° or 60° C., the mixture is filtered, washed with 50 parts by volume of trichlorobenzene, dried carefully, washed with acetone until the trichlorobenzene is totally eliminated, and then dried at 80° C.

59 Parts of a product with the following formula is obtained:

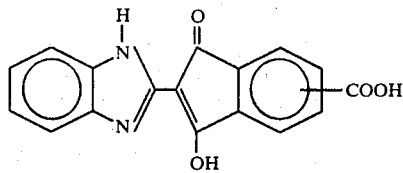

which offers the peaks of infrared absorption expected for a benzimidazolophthalone at 6.17μ and 6.36μ. The elementary analysis accords well with theory:

|  | C % | H % | N % |
| --- | --- | --- | --- |
| Calculated for $C_{17}H_{10}N_2O_4$: | 66.6 | 3.27 | 9.15 |
| Found: | 66.5 | 3.32 | 9.13 |

(1-b) Into 300 parts by volume of nitrobenzene is introduced 30 parts of the product of 1-a and 0.5 part by volume of dimethylformamide. This is heated to 80°-85° C. Then, over 15 minutes, is introduced 20 parts of thionyl chloride. Then the temperature is raised to 150°-155° C. over 45 to 60 minutes and that temperature is maintained for three hours. The mixture is then cooled down to 30°-40° C., filtered and washed with 20 parts by volume of nitrobenzene, and then with acetone, until the nitrobenzene is completely eliminated. After drying at 80° C., there is obtained 27 parts of 2-(benzimidazolyl-2) 1-oxo 3-hydroxyindene 5(6)-carboxylic acid chloride whose structure is confirmed by infrared spectroscopy: disappearance of the COOH peak at 5.85μ and appearance of the COCl peak at 5.65μ.

(1-c) Into 350 parts by volume of nitrobenzene is introduced 24 parts of the product of 1-b, heated to 80°-90° C. and then introduced, over 10 to 15 minutes, a solution of 14 parts of 2,5-dichloro aniline in 12 parts of pyridine. It is heated to 170° C. over one hour and maintained at that temperature for one hour. It is then cooled to 30°-40° C. and then filtered and washed with nitrobenzene, and then with acetone.

There is obtained 28 parts of a yellow pigment with the following formula:

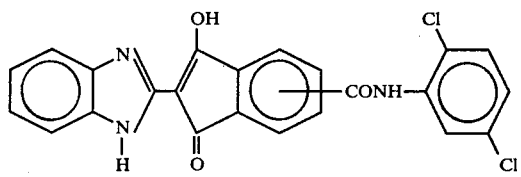

whose chemical structure is confirmed by infrared spectroscopy: disappearance of the COCl peak at 5.65μ, no appearance of the COOH peak at 5.85μ; appearance of the amide peak at 6.1μ and 6.25μ, partly mingled with those of the benzimidazolophthalone configuration. Thermal analysis of this product shows that it withstands treatment at 350° C. for 15 minutes without fusion, change of color or decomposition. All of its analytical characteristics are retained after this treatment. Its coloristic and solidity properties are excellent.

It is possible to cause the physical form of the pigment to develop in the direction of the desired coloristic properties (transparency, opacity and dispersability) by prolonging the heating in nitrobenzene, if necessary, after the reaction is complete and before isolation.

EXAMPLE 2

Into 500 parts by volume of trichlorobenzene is introduced 40 parts of trimellitic anhydride and 27.5 parts of 2-methylbenzimidazole. The mixture is heated to reflux and maintained for three or four hours. After cooling to 80°–85° C., one part by volume of dimethylformamide is added; then 40 parts of thionyl chloride is introduced over 15 minutes and heated to 150°–155° C. over 45 to 60 minutes. That temperature is maintained for 3 hours, then cooled to 30°–40° C. and isolated as in Example 1-b. There is obtained 50 parts of a product that is analytically identical with that in Example 1-b.

EXAMPLE 3

Into 500 parts by volume of trichlorobenzene is introduced 48 parts of trimellitic anhydride, 33 parts of 2-methyl benzimidazole and 6.5 parts of p-toluenesulfonic acid. This is heated to reflux and maintained for three or four hours. After cooling and isolation as in Example 1-a, there is obtained 69 parts of a product identical with that of Example 1-a.

EXAMPLE 4

(4-a) The operation as in Example 1-a was repeated, but using 34.7 parts of 5(6)-chloro 2-methyl benzimidazole instead of 2-methyl benzimidazole. There is obtained 54 parts of a product with the following formula:

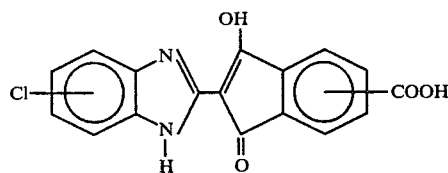

whose spectrum is similar to that of the nonchlorinated product; that is, a COOH peak at 5.85μ and benzimidazolophthalone peaks at 6.1 and 6.28μ.

(4-b) The operation as in Example 1-b was repeated, but replacing the 30 parts of 2-(benzimidazolyl-2) 1-oxo 3-hydroxy indene 5(6)-carboxylic by 33.4 parts of the acid with the above formula. There is obtained 25 parts of 2-[5(6)-chloro benzimidazolyl-2] 1-oxo 3-hydroxy indene-5(6)-carboxylic acid chloride, whose structure is confirmed by infrared spectroscopy; disappearance of the COOH peak at 5.85μ and appearance of the COCl peak at 5.7μ.

(4-c) Into 350 parts by volume of nitrobenzene is introduced 24 parts of the acid chloride of 4-b above and the mixture is heated to 80°–90° C. Then, a solution of 6 parts of aniline in 12 parts of pyridine is introduced, heated to 170° C. over one hour and maintained at that temperature for one hour. After cooling and isolation as in Example 1-c, there is obtained 23 parts of a greenish-yellow pigment having the following formula:

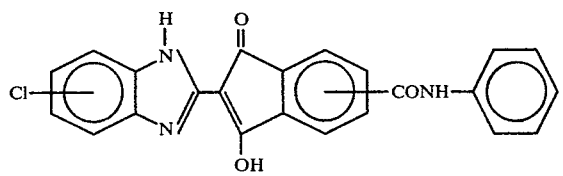

whose spectrum IR is similar to that of the pigment obtained in Example 1-c.

EXAMPLE 5

(5-a) Into 550 parts by volume of trichlorobenzene is introduced 31.5 parts of trimellitic anhydride and 24 parts of a mixture containing about 12 parts of 2,4(2,7)-dimethyl benzimidazole and 12 parts of 2,5(2,6)-dimethyl benzimidazole. The mixture is heated to 170°–175° C. over one-half hour, maintained at that temperature for one and one-half hours, then brought to reflux and maintained at reflux for three or four hours. After isolation as in Example 1-a, there is obtained 37 parts of a mixture in approximately equal parts of the two acids with the following formulas:

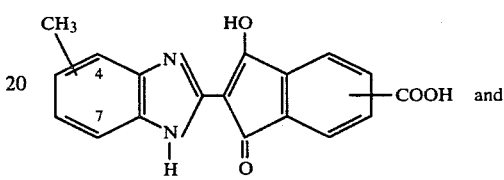

(CH₃ in positions 4 or 7)

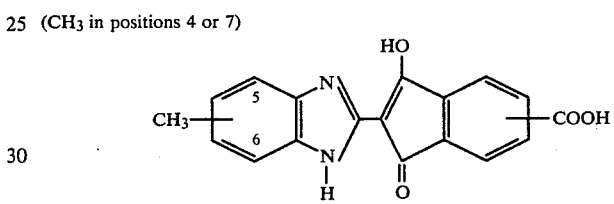

(CH₃ in positions 5 or 6)

The spectrum IR of this product is similar to that of the nonmethylated acid: acid peak split into two at 5.85μ and benzimidazolophthalone peaks at 6.15 and 6.3μ. Its elementary analysis accords well with theory:

|  | C % | H % | N % |
| --- | --- | --- | --- |
| Calculated for $C_{18}H_{12}N_2O_4$: | 67.5 | 3.75 | 8.75 |
| Found: | 67.3 | 3.9 | 8.6 |

(5-b) Into 200 parts by volume of nitrobenzene is introduced 32 parts of the product of 5-a, heated to 80°–85° C. and 0.5 part by volume of dimethylformamide is added. Then, 16 parts of thionyl chloride are added over from 10 to 15 minutes, heated to 150° C. over three-fourths of an hour and maintained at that temperature for three hours. After cooling and isolation as in Example 2-b, there is obtained 25 parts of a mixture of the acid chlorides of the compounds prepared in Example 5-a. Infrared spectrum: peak at 5.7μ (COCl) and disappearance of the peak divided into two at 5.85μ (COOH).

(5-c) Into 300 parts by volume of dichlorobenzene is introduced 25 parts of the product of 5-b and heated to 90°–100° C. Then, a solution of 17.5 parts of 3,5-dicarbethoxy aniline in 100 parts by volume of dichlorobenzene is added over 15 minutes. The mixture is heated to reflux and maintained at reflux for two or three hours. After cooling to 30°–40° C., filtering and washing, there is obtained 36 parts of an orange-colored yellow pigment whose coloristic and solidity properties are excellent and which is made up of a mixture of the compounds having the following formulas:

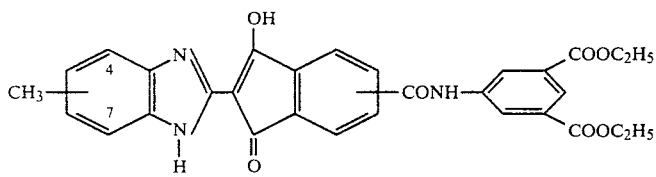

(CH₃ in position 4 or 7); and

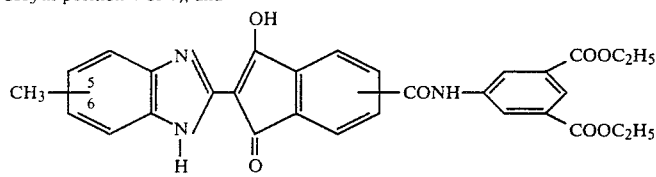

(CH₃ in positions 5 or 6)

EXAMPLES 6 TO 28

The following Table A summarizes other examples of monoamide pigments (formula I) of the invention, obtained, as in the preceding examples, by condensation of the amine indicated in the third column with the acid chloride prepared from the acid obtained by condensing the trimellitic anhydride and the benzimidazole indicated in the second column.

ple 1-b, heated to 80°–90° C. and a solution made up of 3.7 parts of paraphenylenediamine, 5.4 parts of pyridine and 150 parts of nitrobenzene is added over 15 minutes. The mixture is heated to 150° C. over 45 to 60 minutes, maintained at that temperature for two hours and then heated to 165°–170° C. over one hour. After cooling, filtering and washing, there is obtained 23 parts of a greenish-yellow pigment having the following formula:

TABLE A

| Example | Benzimidazole | Amine | Shade |
|---|---|---|---|
| 6 | 2-Methyl benzimidazole | aniline | yellow |
| 7 | 2-Methyl benzimidazole | p-chloro-aniline | " |
| 8 | 2-Methyl benzimidazole | 2,4,5-trichloro aniline | " |
| 9 | 2-Methyl benzimidazole | 2-methyl 5-chloro aniline | " |
| 10 | 2-Methyl benzimidazole | o-toluidine | " |
| 11 | 2-Methyl benzimidazole | p-anisidine | greenish yellow |
| 12 | 2-Methyl benzimidazole | 3,5-dimethyl aniline | yellow |
| 13 | 2-Methyl benzimidazole | 2-nitro 4-methyl aniline | orange |
| 14 | 2-Methyl benzimidazole | p-amino-acetanilide | greenish yellow |
| 15 | 2-Methyl benzimidazole | 2,5-dimethoxy 4-benzolyamino aniline | dark yellow |
| 16 | 2-Methyl benzimidazole | α-amino-anthraquinone | orange-brown |
| 17 | 2-Methyl benzimidazole | 3-amino 1,2,4-triazole | reddish yellow |
| 18 | 2-Methyl benzimidazole | cyclohexylamine | yellow |
| 19 | 2,5(2,6)-Dimethyl benzimidazole | 2,5-dichloro aniline | orange-yellow |
| 20 | 2,5(2,6)-Dimethyl benzimidazole | 2-methyl 4-chloro aniline | orange |
| 21 | 2,5(2,6)-Dimethyl benzimidazole | 4-ethoxy aniline | orange-yellow |
| 22 | 2,5,6-Trimethyl benzimidazole | o-toluidine | ochre yellow |
| 23 | 50-50 mixture of 2,4(2,7)-dimethyl benzimidazole and 2,5(2,6)-dimethyl benzimidazole | 2-nitro 4-methyl aniline | orange-red |
| 24 | 50-50 mixture of 2,4(2,7)-dimethyl benzimidazole and 2,5(2,6)-dimethyl benzimidazole | 3(5)-phenyl 5(3)-amino pyrazole | orange |
| 25 | 50-50 mixture of 2,4(2,7)-dimethyl benzimidazole and 2,5(2,6)-dimethyl benzimidazole | 2-amino benzothiazole | orange-yellow |
| 26 | 5(6)-Chloro 2-methyl benzimidazole | 3-amino 1,2,4-triazole | yellow |
| 27 | 5(6)-Nitro 2-methyl benzimidazole | 2,4-dimethyl aniline | yellow |
| 28 | 5(6)-Nitro 2-methyl benzimidazole | p-amino-diphenyl-amine | greenish yellow |

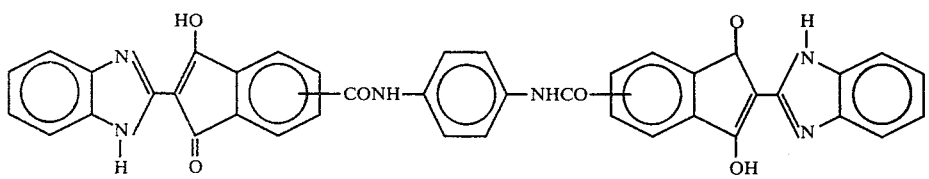

EXAMPLE 29

Into 350 parts by volume of nitrobenzene is introduced 22 parts of the acid chloride prepared as in Exampossessing excellent solidities.

EXAMPLES 30 TO 39

The following Table B summarizes other examples of diamide pigments according to the invention, obtained as in Example 29, by replacing the acid chloride in accordance with Example 1-b by an equimolar quantity of the acid chloride prepared from the acid resulting from the condensation of the trimellitic anhydride with the benzimidazole indicated in the second column and/or by replacing the paraphenylene-diamine by an equimolar quantity of the diamine indicated in the third column. These pigments offer good coloristic properties and excellent solidities.

TABLE B

| Example | Benzimidazole | Diamine | Shade |
|---|---|---|---|
| 30 | 2-Methyl benzimidazole | chloro-p-phenylene-diamine | yellow |
| 31 | 2-Methyl benzimidazole | 4,4′-diamino diphenyl | ochre yellow |
| 32 | 2-Methyl benzimidazole | 2,6-diamino pyridine | greenish yellow |
| 33 | 2-Methyl benzimidazole | 1,5-diamino-naphthalene | ochre |
| 34 | 2-Methyl benzimidazole | diamino-durene | yellow |
| 35 | 2,5(2,6)-dimethyl benzimidazole | 4,4′-diamino diphenyl | " |
| 36 | 50-50 mixture of 2,4(2,7)-dimethyl benzimidazole and 2,5(2,6)-dimethyl benzimidazole | 4,4′-diamino diphenyl-sulfone | brown |
| 37 | 50-50 mixture of 2,4(2,7)-dimethyl benzimidazole and 2,5(2,6)-dimethyl benzimidazole | 4,4′-diamino diphenylurea | brownish yellow |
| 38 | 5(6)-Chloro 2-methyl benzimidazole | 4,4′-diamino diphenyloxide | greenish yellow |
| 39 | 5(6)-Methoxy 2-methyl benzimidazole | p-phenylene-diamine | yellow |

What is claimed is:

1. A phthalone represented by one of the following formulas:

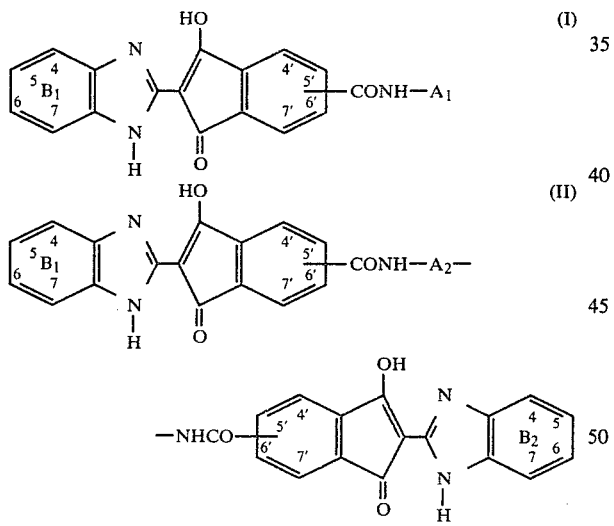

in which $A_1$ represents:
- an aliphatic or alicyclic radical,
- a diphenyl or naphthalene radical,
- an anthraquinone radical or an anthraquinone radical substituted by one or two chlorine or bromine atoms,
- a benzene radical or a benzene radical bearing up to five non-solubilizing substituents selected from halogen, lower alkyl, lower alkoxy, nitro, cyano, acetylamino, benzoylamino, phenylaminocarbonyl and phenylamino, or
- a pyridine, 1,2,4-triazole, 3(5)phenyl-5(3)pyrazole or benzothiazole radical;

$A_2$ represents:
- a benzene radical or a benzene radical bearing up to four substituents selected from chlorine, cyano, bromine, methoxy, ethoxy and methyl, or
- a pyridine, diphenyl, naphthalene, anthraquinone, diphenylamine, diphenyloxide, diphenylsulfide, benzanilide, benzophenone, diphenylurea, diphenylsulfone or diphenylsulfoxide radical;

and each of the benzene nuclei $B_1$ and $B_2$ can bear one or two substituents selected from halogen, lower alkyl, lower alkoxy, nitro, phenyl, alkylcarbonylamino containing 2 to 4 carbon stoms, benzoylamino and benzoylamino bearing one or two nitro groups, or be coupled with another benzene nucleus.

2. A phthalone as claimed in claim 1 wherein the —CONH—$A_1$ and —CONH—$A_2$—NHCO— radicals are fixed in positions 5′ or 6′.

3. A phthalone as claimed in claim 2 which each of the nuclei $B_1$ and $B_2$ is unsubstituted or is substituted by a chlorine atom or by one or two methyl groups.

4. A phthalone as claimed in claim 1 in which each of the nuclei $B_1$ and $B_2$ is unsubstituted or is substituted by a chlorine atom or by one or two methyl groups.

5. A phthalone as claimed in claims 1, 2, 3 or 4 in which $A_1$ is a substituted phenyl radical and $A_2$ is a p-phenylene or chloro-p-phenylene radical.

6. A mixture of phthalones as claimed in claim 5.

7. A mixture of phthalones as claimed in claims 1, 2, 3 or 4.

8. A compound represented by the formula:

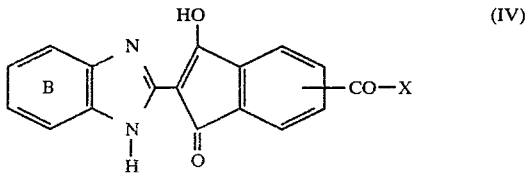

in which X represents a hydroxy group or a chlorine or bromine atom and the nucleus B can bear one or two substituents selected from halogen, lower alkyl, lower alkoxy, nitro, phenyl, alkylcarbonylamino containing 2 to 4 carbon atoms, benzoylamino and benzoylamino bearing one or two nitro groups, or is coupled with another benzene nucleus.

9. A phthalone as claimed in claims 1, 2, 3 or 4 in which $A_1$ is the 1,2,4-triazole-3-yle radical.

10. A phthalone as claimed in claim 1 wherein:
$A_1$ represents a benzene radical or a benzene radical bearing up to five non-solubilizing substituents selected from halogen, lower alkyl, lower alkoxy, nitro, cyano, acetylamino and benzoylamino; and $A_2$ represents a benzene radical or a benzene radical bearing up to four substituents selected from chlorine, cyano, bromine, methoxy, ethoxy and methyl, or a radical of the formula:
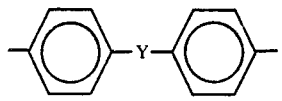
wherein Y is a direct linkage, an oxygen or sulfur atom or a NH, CO, NHCO, NHCONH, SO or $SO_2$ linkage.
* * * * *